(12) United States Patent
Powell

(10) Patent No.: US 6,589,202 B1
(45) Date of Patent: Jul. 8, 2003

(54) METHOD AND APPARATUS FOR TRANSDERMALLY SAMPLING OR ADMINISTERING A SUBSTANCE TO A PATIENT

(75) Inventor: Kenneth G. Powell, Raleigh, NC (US)

(73) Assignee: Becton Dickinson and Company, Franklin Lakes, NY (US)

( * ) Notice: Subject to any disclaimer, the term of this patent is extended or adjusted under 35 U.S.C. 154(b) by 0 days.

(21) Appl. No.: 09/606,907

(22) Filed: Jun. 29, 2000

(51) Int. Cl.[7] ................................................. A61M 1/00
(52) U.S. Cl. ..................................... 604/27; 604/890.1
(58) Field of Search ............................... 604/20, 22, 46, 604/21, 47, 48, 890.1, 117; 606/183, 186; 424/9.8, 9.81, 441; 600/556, 306, 362; 128/114.1, 907

(56) References Cited

U.S. PATENT DOCUMENTS

| 5,250,023 A |   | 10/1993 | Lee et al. |
| 5,533,972 A | * | 7/1996 | Gyory et al. ................. 604/20 |
| 5,879,326 A |   | 3/1999 | Godshall et al. |
| 5,964,729 A |   | 10/1999 | Choi et al. |
| 6,050,988 A | * | 4/2000 | Zuck ....................... 604/890.1 |
| 6,083,196 A | * | 7/2000 | Trautman et al. .............. 604/46 |

FOREIGN PATENT DOCUMENTS

| WO | WO 95-12357 | 5/1995 |
| WO | WO 97-03718 | 2/1997 |
| WO | WO 97/48440 | 12/1997 |

* cited by examiner

Primary Examiner—Manuel Mendez
(74) Attorney, Agent, or Firm—Venable; Richard Schmidt; Jeffri A. Kaminski

(57) ABSTRACT

A device for delivering or withdrawing a substance from a patient includes a support member, a skin penetrating device and an advancing assembly for advancing the skin penetrating device to an operating position. The advancing assembly includes a supply spool for supporting a web having the skin penetrating devices attached thereon and a take up spool for receiving the web with the spent skin penetrating devices. The support has a bottom wall with at least one opening for exposing the skin penetrating device for penetrating the skin of a patient. In one embodiment the skin penetrating devices are micro needles having a length of about 50–2000 microns.

38 Claims, 7 Drawing Sheets

METHOD AND APPARATUS FOR TRANSDERMALLY SAMPLING OR ADMINISTERING A SUBSTANCE TO A PATIENT

FIELD OF THE INVENTION

The present invention relates to a method and apparatus for withdrawing a sample from or delivering a substance transdermally to a patient. More particularly, the invention is directed to a method and apparatus for withdrawing a sample from or delivering a substance to successive patients using a device having a plurality of skin penetrating devices.

BACKGROUND OF THE INVENTION

Drugs and various pharmaceutical agents are delivered to the body by many known methods. One method that is often used for the subcutaneous delivery uses a needle or other cannula. The use of a cannula is an effective method of delivering a drug. However, the pain typically experienced by the patient has prompted the development of alternative methods for delivering drugs.

Various devices have been proposed for the transdermal delivery of substances to the body and for withdrawing a substance from the body in a manner that is less painful to the patient. Transdermal delivery devices are often used to provide a sustained release of the substance to maintain a desired rate of delivery. Many transdermal delivery devices do not administer the drug at a sufficient rate to be used effectively. Moreover, many drugs can not be delivered transdermally since the drugs are not able to pass through the protective skin layers.

The skin is made up of several layers with the upper composite layer being the epithelial layer. The outermost layer of the skin is the stratum corneum that has well known barrier properties to prevent molecules and various substances from entering the body and analytes from exiting the body. The stratum corneum is a complex structure of compacted keratinized cell remnants having a thickness of about 10–30 microns. The stratum corneum forms a waterproof membrane to protect the body from invasion by various substances and the outward migration of various compounds. The natural impermeability of the stratum corneum prevents the administration of most pharmaceutical agents and other substances through the skin. Numerous methods and devices have been proposed to enhance the permeability of the skin and to increase the diffusion of various drugs through the skin to be utilized by the body.

One type of device that has gained attention in recent times is the micro device that is able to penetrate the outer layers of the skin with less pain or discomfort than a standard cannula. These micro devices typically have needles that are a few microns to several hundred microns in length. The micro devices for delivering drugs through the skin form micro pores or cuts through the stratum corneum. By penetrating the stratum corneum and delivering the drug to the skin in or below the stratum corneum, many drugs can be effectively administered. The devices for penetrating the stratum corneum generally include a plurality of micron size needles or blades having a length to penetrate the stratum corneum without passing completely through the epidermis. Examples of these devices are disclosed in U.S. Pat. No. 5,879,326 to Godshall et al.; U.S. Pat. No. 5,250,023 to Lee et al., and WO 97/48440.

Transdermal drug delivery is also known to use pulsed laser light to ablate the stratum corneum without significant ablation or damage to the underlying epidermis. A drug is then applied to the ablated area and allowed to diffuse through the epidermis.

The delivery of drugs through the skin can be enhanced by either increasing the permeability of the skin or increasing the force or energy used to direct the drug through the skin. One example of a method for increasing the delivery of drugs through the skin is iontophoresis. Iontophoresis generally applies an external electrical field to ionize the drug, thereby increasing the diffusion of the drug through the skin. Iontophoresis can be difficult to control the amount and rate of drug delivery. Under some circumstances, iontophoresis can cause skin damage depending on the extent of ionization, the energy applied to ionize the drug and duration of the treatment.

Sonic, and particularly ultrasonic energy using a piezoelectric crystal, has also been used to increase the diffusion of drugs through the skin. Although numerous efforts to enhance drug delivery using sonic energy have been proposed, the results generally show a low rate of drug delivery.

The prior methods and apparatus for the transdermal administration of drugs can be cumbersome to use and have exhibited limited success. Accordingly, a continuing need exists in the industry for an improved device for the administration of various drugs and other substances thought the skin of a patient.

SUMMARY OF THE INVENTION

The present invention is directed to a method and apparatus for withdrawing a substance or delivering a substance to a patient, such as a drug, vaccine or other pharmaceutical agent. In particular, the invention is directed to a method and apparatus for withdrawing a substance though the skin or delivering a substance to the skin to a sufficient depth where the substance can be absorbed and utilized by the body. In embodiments of the invention, the substance to be delivered is a dry drug that can be reconstituted and introduced into the intradermal tissue below the stratum corneum where the substance can be absorbed.

Accordingly, a primary object of the invention is to provide a method and apparatus for efficiently withdrawing a substance or administering a substance transdermally to several patients without risk of cross contamination between patients.

Another object of the invention is to provide a device having a plurality of skin penetrating devices for penetrating the stratum corneum of the skin and withdrawing a substance from or delivering a substance to the skin.

A further object of the invention is to provide a device for delivering a vaccine where the device has a plurality of skin penetrating devices that can be sequentially presented for successive delivery to several patients.

Another object of the invention is to provide a method and apparatus for transdermally withdrawing a sample from a patient or delivering a substance to a patient using a device having a plurality of spaced apart needle arrays where each needle array can be advanced to an operating position for each patient.

Another object of the invention is to provide a device for delivering a substance to a patient without requiring a separate reconstituting or reformulation step.

Still another object of the invention is to provide a transdermal sampling or delivery device having a web with a plurality of spaced-apart skin penetrating devices and an advancing device to present a clean and sterile skin penetrating device for sampling or delivering a substance to successive patients.

A further object of the invention is to provide a device for the transdermal sampling or delivery of a substance to a patient where the device has a plurality micro needle arrays and a dried substance on the micro needles where the device can deliver the substance to successive patients.

These and other objects of the invention are substantially attained by providing a device for sampling or delivering a substance to a patient where the device has a support with a bottom wall. The support houses a flexible web having a plurality of skin penetrating devices attached to the web. The web is mounted within the support in a manner to supply the web and the skin penetrating devices across an outer face of the bottom wall with the skin penetrating devices facing outwardly from the support in a position to be available for penetrating the skin of a patient. Generally an advancing device is included to advance the web and the skin penetrating devices though the support. The skin penetrating device has a length sufficient to penetrate at least the stratum corneum of the skin. In one embodiment the skin penetrating device pierces the stratum corneum.

The objects and advantages of the invention are further attained by providing a delivery device for administering a substance through the skin of a patient. The device comprises a support having a top end, a bottom end and a bottom wall at the bottom end. A supply member supporting a web with a plurality of skin penetrating devices is mounted within the support. Each of the skin penetrating devices has a substance to be delivered to the patient. An advancing assembly is included to advance the web and the skin penetrating members incrementally across the bottom wall to expose the skin penetrating members and position the skin penetrating members in a position for delivering the substance to the patient. A recovery device is provided to receive the web after the skin penetrating member is used.

Another object of the invention is to provide a method of withdrawing or administering a substance through the skin of a patient, the method comprising providing a device having a support with a top end, a bottom end, and a bottom wall, a supply member for supporting a web having a plurality of skin penetrating members, an advancing assembly for incrementally advancing the web from the supply member across the bottom end of the support to a recovery member, wherein each skin penetrating member is available for penetrating the skin of a patient when positioned on the bottom wall of the support, the method comprising advancing the web to expose a penetrating member on the bottom wall, pressing the skin penetrating member against the skin of a patient, and delivering or withdrawing a substance to the patient.

The objects, advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings in which.

DETAILED DESCRIPTION OF THE PREFERRED EMBODIMENTS

The present invention is directed to a device for monitoring, withdrawing, sampling or administering a substance though the skin of a patient. More particularly, the invention is directed to a device and to a method for sequentially sampling or delivering a substance to a plurality of patients into or below the stratum corneum. As used herein, the term penetrate refers to entering a layer of the skin without passing completely through the skin. Piercing refers to passing completely through a layer of the skin.

The device and method of the present invention in one embodiment of the invention are particularly suitable for use in delivering or administering various substances, including pharmaceutical agents, to a patient, and particularly to a human patient. As used herein, a pharmaceutical agent includes a substance having biological activity that can be delivered through the body membranes and surfaces, and particularly the skin. Examples include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally to a patient include proteins, peptides and fragments thereof. The proteins and peptides can be naturally occurring, synthesized or recombinantly produced.

The primary barrier properties of the skin including the resistance to drug penetration reside in the outermost layer of the skin, referred to as the stratum corneum. Once a drug or other substance penetrates below the stratum corneum, there is substantially less resistance to permeation into the subsequent layers of the skin and eventual absorption by the body. Thus, delivery of a substance below the stratum corneum can be an effective system for administering some substances, and particularly some vaccines, to the body. The present invention is primarily directed to a device and method for withdrawing or delivering a substance, and particularly a pharmaceutical agent, into or below the stratum corneum for administering the substance or pharmaceutical agent to the patient. In one embodiment, the device and method of the invention pierce the stratum corneum to target the tissue layers below the stratum corneum.

Figure 1:
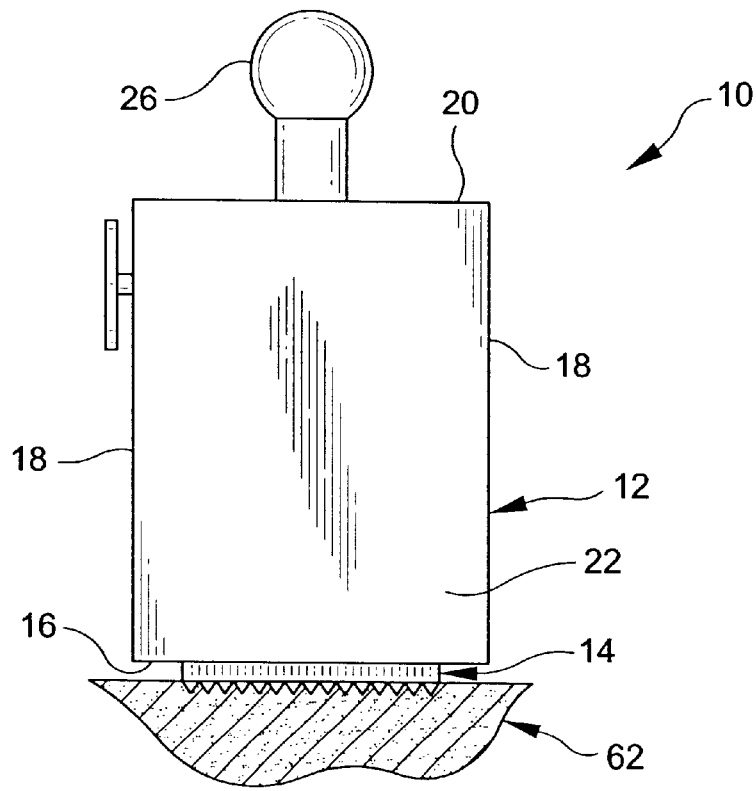
FIG. 1 is a front view of a sampling or delivery device in accordance with a first embodiment of the invention.

Referring to FIG. 1, the device 10 includes a support 12 and a plurality of skin penetrating devices 14. Support 12 in the embodiment illustrated includes a bottom wall 16, side walls 18 and a top wall 20. A front wall 22 and a rear wall 24 extend between the side walls 18 to from an enclosed housing. Top wall 20 includes a handle 26 for manipulating the device 10.

Figure 2:
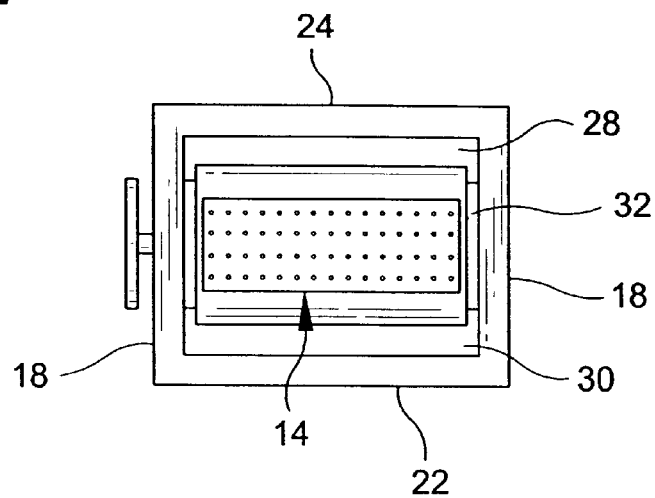
FIG. 2 is a bottom view of the device of FIG. 1 showing the needle array and the opening in the bottom of the support.

Bottom wall 16 includes at least one opening and preferably a first opening 28 and a second opening 30 that are spaced apart in a side-by-side arrangement as shown in FIG. 2. First and second openings 28 and 30 have a length and width to allow skin penetrating devices 14 to pass through without interfering with or damaging the skin penetrating devices 14.

Figure 3:
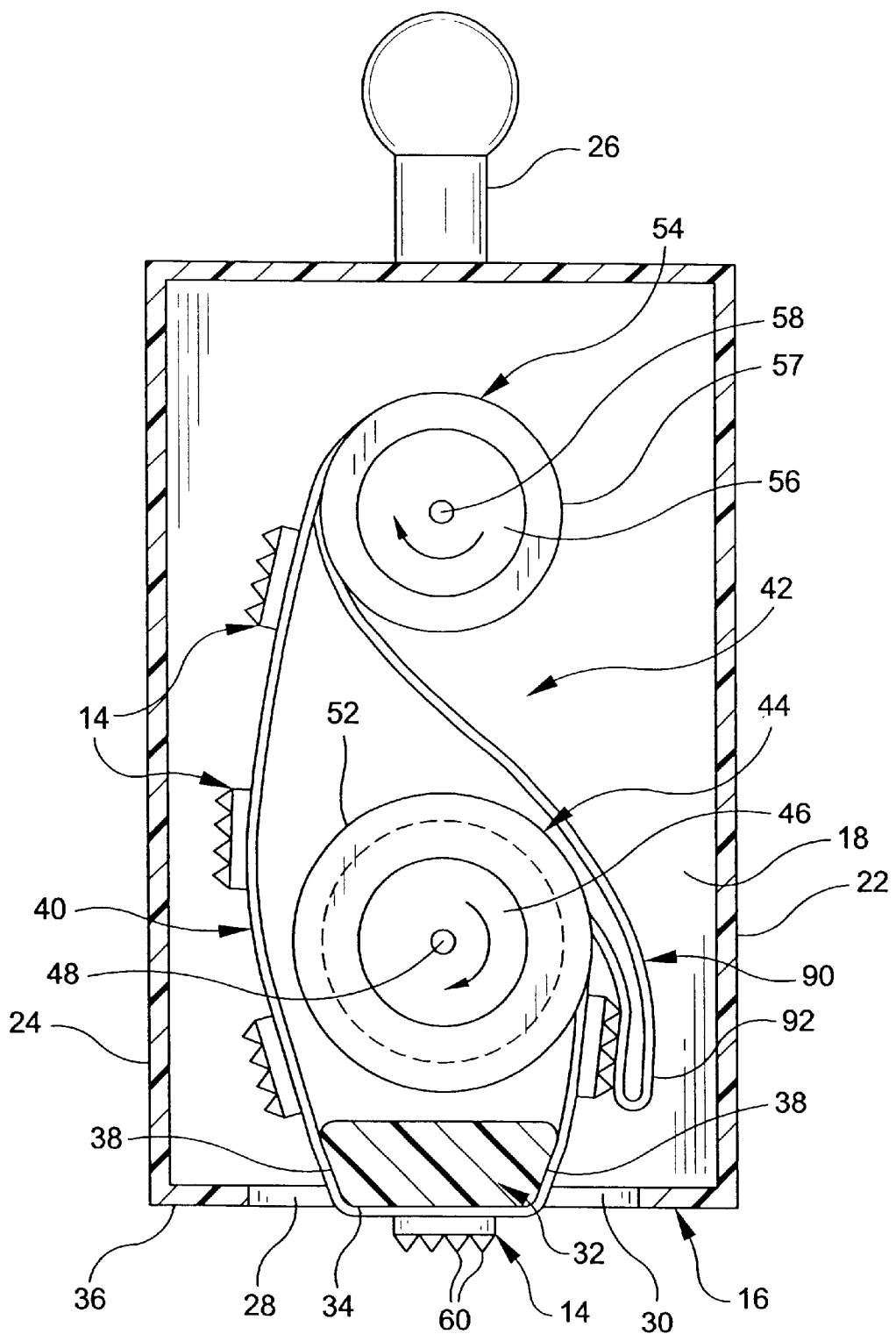
FIG. 3 is a side view in cross section of the sampling or delivery device of FIG. 1 showing the web, skin penetrating devices, supply member and take-up member.

As shown in FIG. 3, a platen 32 is positioned between the openings 28 and 30. Generally, platen 32 is coupled to bottom wall 16 and to side walls 18 to secure platen 32 in place. As shown, openings 28 and 30 have a generally longitudinal length extending a substantial portion of the width of bottom wall 16. In further embodiments of the invention, openings 28 and 30 can have a length equal to the width of bottom wall 16.

Platen 32 has a bottom face 34 that is substantially parallel to and flush with the bottom face 36 of bottom wall 16. Platen 32 has a thickness greater than the thickness of bottom wall 16 to enable the device 10 to absorb the force necessary for the skin penetrating devices 14 to penetrate the skin as discussed hereinafter in greater detail. In the embodiment shown, platen 32 has a generally trapezoidal shape to guide skin penetrating devices 14 through openings 28 and 30 of bottom wall 16 of device 10. In the embodiment illustrated, platen 32 has inclined side walls 38 that diverge outwardly from openings 28 and 30 to assist in guiding the skin penetrating devices 14 to an operating position.

Figure 4:
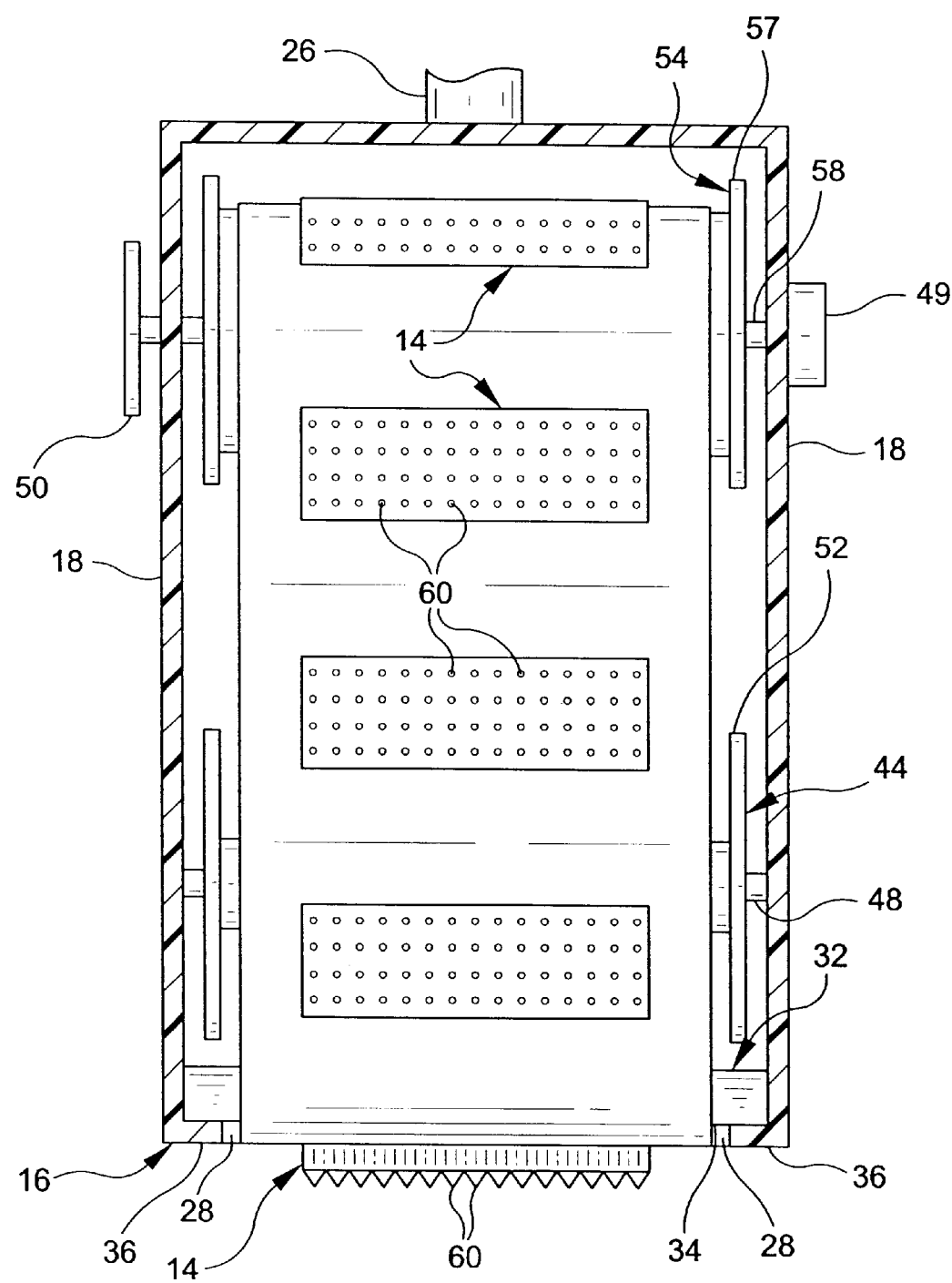
FIG. 4 is a rear view in cross section of the sampling or delivery device of FIG. 1 showing the supply of skin penetrating devices.
Figure 5:
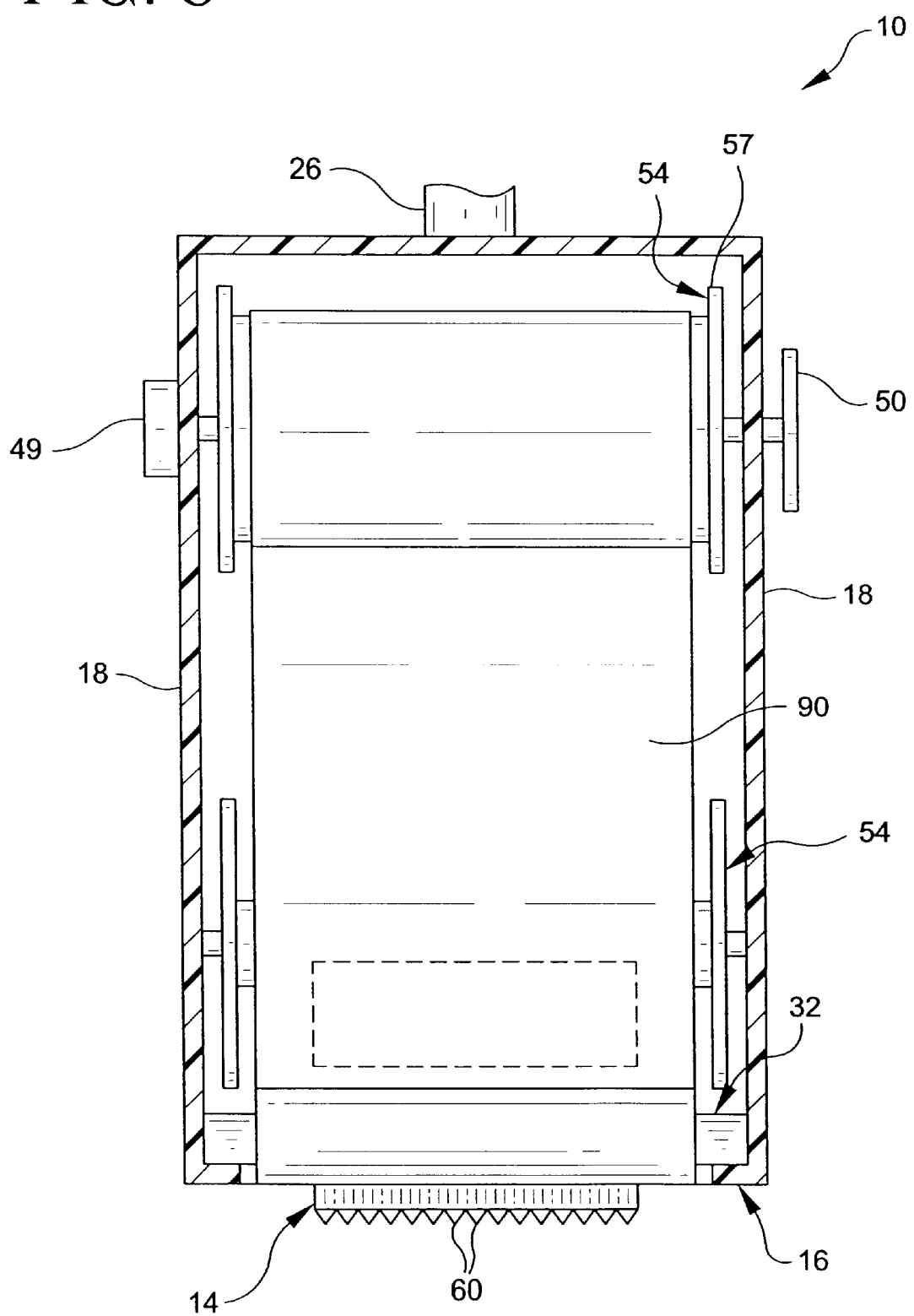
FIG. 5 is a front view in cross section of the sampling or delivery device of FIG. 1 showing the release liner and take-up member.

Referring to FIGS. 3–4, a plurality of the skin penetrating devices 14 mounted on a continuous web 40. As shown in FIG. 3, skin penetrating devices 14 are spaced apart on an outer face of web 40 and are oriented facing in a generally outward direction. The web 40 is flexible member that can be rolled and fed from a suitable supply though openings 28 and 30 in bottom wall 16 of support 12. Web 40 can be made of a suitable material that has sufficient strength to support skin penetrating devices 14 and can feed the devices to an operating position on bottom face 34 of platen 32. In preferred embodiments of the invention, web 40 has a longitudinal length to be able to support a desired number of skin penetrating devices 14. The number of skin penetrating devices 14 that are mounted on web 40 will vary depending on the intended use of the device 10 and the dimensions of support 12.

Skin penetrating devices 14 are preferably spaced apart a distance to enable each device 14 to be used independently of each other when positioned on platen 32. Therefore, in the illustrated embodiment, skin penetrating devices 14 are spaced a distance so that only a single skin penetrating device 14 is able to contact the skin of a patient when in use.

In one embodiment of the invention, device 10 is to be used for delivering a vaccine to several patients in sequential order. Therefore, it is desirable to have web 40 be of sufficient length to support a number of skin penetrating devices 14 to increase the efficiency of the device. The number of skin penetrating devices 14 on the web will also depend on the thickness and dimensions of the skin penetrating devices so that the devices can be stored within the device 10.

As shown in FIG. 4, skin penetrating devices 14 have a generally rectangular shape. The actual shape of skin penetrating devices 14 will depend at least in part on the method of manufacturing the devices 14 and the required dimensions for sampling or delivering the substance to the patient. In a further embodiment of the invention the skin penetrating device can have a generally square shape or a round shape.

Referring to FIGS. 3 and 4, an advancing and feeding assembly 42 is included to advance web 40 and skin penetrating devices 14 through device 10. Advancing assembly 42 includes a supply member 44, which in the embodiment illustrated, is a supply spool 46. Alternatively, supply member 44 can be a container for supporting the web 40 until fed through the device. Web 40, in one embodiment, can be folded in an accordion fashion. As shown in FIG. 4, supply spool 46 is mounted on a shaft 48 for rotation with respect to support 12. Spool 46 and shaft 48 are mounted for rotating on an axis substantially parallel to the plane of bottom wall 16. In one embodiment of the invention, shaft 48 is coupled to side walls 18 and is rotatable with respect to side walls 18.

Spool 46 has a substantially cylindrical shape with a flange 52 at each end to position web 40 on spool 46. Spool 46 has a dimension to be able to support a designated length of web 40 and skin penetrating devices 14. In this embodiment, web 40 with skin penetrating devices 14 mounted thereon is wound onto spool 40 in a spiral fashion.

A receiving member 54 is also provided in support 12 to receive web 40 after web 40 and skin penetrating devices 14 have been used. In the embodiment illustrated, the receiving member 54 is a take-up spool 56 having flanges 57 at each end. As shown in FIG. 4, take-up spool 56 is mounted on a shaft 58 that is coupled to side walls 18. Take up spool 56 is rotatable with respect to side wall 18 about an axis substantially parallel to the axis of rotation of supply spool 46. Preferably, shaft 58 has a length to extend through at least one of the side walls 18 and is coupled to a handle 50 or other suitable device for rotating shaft 58 and spool 56. Generally, shaft 58 is mounted on a suitable bearing that is coupled to side walls 18. In one embodiment, shaft 58 is coupled to an anti-reverse mechanism 49, such as a ratchet assembly.

Skin penetrating device 14 in embodiments of the invention includes a plurality of skin penetrating members 60. In a preferred embodiment of the invention, the skin penetrating members 60 are needles, blades, lancets or microtubes that are able to penetrate the skin to a desired depth. In the embodiment of FIG. 1, the skin penetrating members 60 are microneedles arranged in an array and have a length to penetrate the skin to a depth sufficient to withdraw or sample or deliver a substance. The actual length of the skin penetrating devices can vary to optimize the delivery or sampling of the particular substance. For example, the skin penetrating members for administering a vaccine can have a length to pass through the stratum corneum into the cells in the skin to generate the desired immune response.

The device 10 is assembled by mounting supply spool 46 and take up spool 56 in support 12. Web 40 and skin penetrating devices 14 are fed from supply spool 46 through first opening 28 in bottom wall 16. Web 40 is then directed across a bottom face 36 of platen 32 with skin penetrating devices 14 facing outward in a generally downward direction as show in FIG. 3. Web 40 is fed back into the support 12 through second opening 30 in bottom wall 16 and onto take up spool 56.

Handle 50 is rotated to advance web 40 to present a skin penetrating device 14 to an operating position on bottom face 34 of platen 32. Device 10 and skin penetrating device 14 is then pressed against the skin 62 of a patient with sufficient pressure to penetrate skin 62 as shown in FIG. 1. Device 10 is held in place on skin 62 for sufficient time to either withdraw a sample of a substance or to deliver a substance. After the appropriate length of time, device 10 is removed from skin 62. Handle 50 is then rotated to advance web 40 to carry the spent skin penetrating device 14 back into support 12 onto take-up spool 56 and to advance a clean skin penetrating device 14 into the operating position on platen 32. Preferably, the skin penetrating members 14 are spaced apart a distance so that a single skin penetrating member 14 is exposed on platen 32 of support 12 and the remaining skin penetrating devices 14 are contained in support 12 to prevent or reduce the risk of cross contamination.

In a preferred embodiment, a cover sheet 90 overlies skin penetrating devices 14 on supply spool 46 to protect skin penetrating devices 14 during storage. Sheet 90 is peeled from web 40 and skin penetrating devices 14 as web 40 is unwound from supply spool 46 to maintain each skin penetrating device in a clean and sterile condition until carried to the operating position on platen 32. As shown in FIG. 3, sheet 90 is fed onto take-up spool 56 with web 40 and spent skin penetrating devices. In this embodiment, the underside 92 of sheet 90 that contacts skin penetrating devices 14 on supply spool 46 is fed to take-up spool 56 so that underside 92 contacts the spent skin penetrating devices 14.

The assembly of FIG. 1 exposes the patient to a single skin penetrating device 14. Accordingly, platen 32 is a width sufficient to support a single skin penetrating device 14 and skin penetrating devices are spaced apart a distance so that a single skin penetrating device is in an operating position. In alternative embodiments of the invention, the device can have a platen of sufficient width to support more than a single skin penetrating device at a time. This arrangement can be desirable where the amount of the substance to be delivered or withdrawn from the patient can not be attained using a single skin penetrating device and where two or more substances are to be delivered simultaneously.

Figure 6:
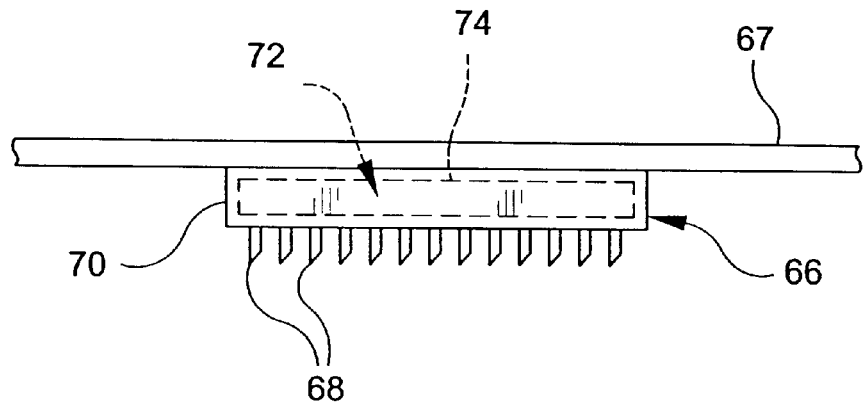
FIG. 6 is side view of the web of skin penetrating devices in a second embodiment of the invention.

In the embodiment of FIG. 6, the skin penetrating device 66 mounted on a web 67, is an array of needles 68 attached to a base 70. Base 70 is mounted on a web 67 as in the embodiment of FIGS. 1–5. The array includes a plurality of hollow needles 68 extending from base 70. The needles 68 can be about 25 to about 35 gauge and can have a length of about 250 to about 2000 microns. Each of the needles 68 includes a passage or opening passing through the length of the needle. The passage in the needles communicates with a central chamber 72. In one embodiment of the invention, central chamber 72 can include an absorbent material 74 for supplying a substance or for absorbing a substance when the device is used for withdrawing a sample from a patient. The absorbent material can be, for example, a cellulose material or gel as known in the art. The passages have a diameter sufficient to allow a fluid to pass through the needles at a suitable rate to deliver the substance to the skin from the central chamber or draw a fluid being withdrawn from the patient. The dimensions of the openings will depend on the substance being administered or withdrawn and the desired flow rate of the substance. The hollow passages in the needles are generally sufficient to allow the fluid sample to be drawn into the needles by the surface tension of the fluid.

Figure 7:
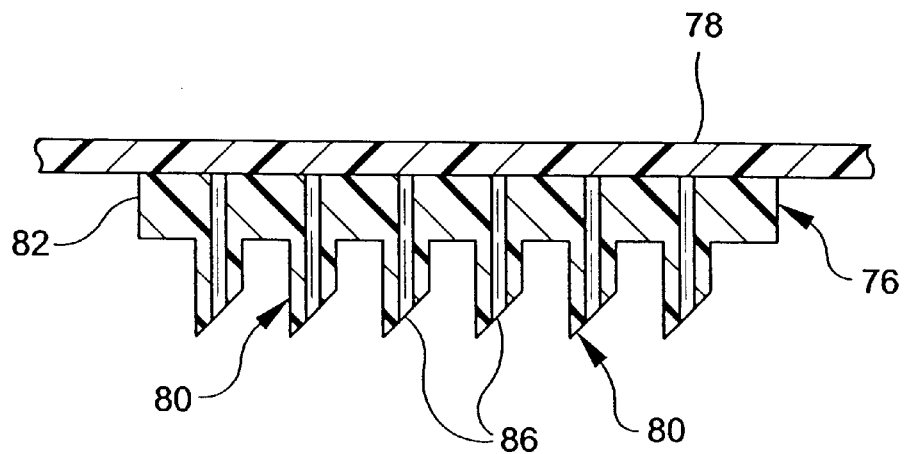
FIG. 7 is a side view in cross section showing the skin penetrating members in a further embodiment of he invention.

Referring to FIG. 7, a further embodiment of the skin penetrating device 76 is shown attached to the web 78. In this embodiment, the skin penetrating device 76 is an array of microneedles 80 machined from a silicon substrate 82. The microneedles 80 have a generally square cross-section and a beveled tip 84. A hollow passage 86 is machined in the needles 80 and extends axially through the needles 80 as shown. The array is mounted on web 78 so that hollow passages 86 form a reservoir for withdrawing a sample from a patient or for storing a substance until delivered to the patient.

In the embodiment shown in FIG. 1, skin penetrating member 60 is preferably a microneedle formed from a substrate such as a silicon wafer or plastic substrate. The microneedles can be integrally formed with a base of the substrate by suitable manufacturing methods such as stereolithography or etching methods as known in the art.

Device 10 is generally made from a plastic material that is non-reactive with the substance being administered. Suitable plastic materials include, for example, polyethylene, polypropylene, polyesters, polyamides and polycarbonates as known in the art. The skin penetrating devices can be made from various materials as known in the art. For example, skin penetrating devices can be made from silicon, stainless steel, tungsten steel, alloys of nickel, molybdenum, chromium, cobalt, and titanium, ceramics, glass, polymers and other non-reactive metals, and alloys thereof.

The length and thickness of the skin penetrating members are selected based on the particular substance being administered, the thickness of the skin in the location where the device is to be applied and the desired depth of penetration. In one embodiment, the skin penetrating members are needles that pierce the stratum corneum to penetrate the epidermis. The needles can have a length for penetrating the skin to a depth of up to about 2000 microns. Suitable needles have a length of about 50 to 2000 microns. Typically, the needles have a length of about 50 to about 1000 microns, and generally in the range of about 250 to 500 microns. The needles in the illustrated embodiment have a generally conical shape. In alternative embodiments, the needles can be triangles, flat blades or pyramids. Typically, the microneedles are perpendicular to the plane of the device. The width of the needles can be about 15 to 40 gauge to obtain optimum penetration of the skin.

As shown in FIG. 4, the needles are typically spaced apart uniformly in rows and columns to form an array for contacting the skin and penetrating the stratum corneum. The spacing between the needles can be varied depending on the substance being administered either on the surface of the skin or within the tissue of the skin. Typically, the needles are spaced a distance of about 0.05 mm to about 5 mm.

In a preferred embodiment, a dried or lyophilized pharmaceutical agent is provided on the needles to deliver the agent to the patient. The dried pharmaceutical agent can be applied as a coating on the needles or on the bottom surface of the skin penetrating device between the needles.

Typically, the needles are uniformly spaced apart to form an array and have a substantially uniform length and width. In a further embodiment, the needles have varying lengths to penetrate the skin at different depths. A needle device with needles of different lengths is particularly effective in delivering a vaccine into the cells into or below the stratum corneum to increase the immunological efficiency of the vaccine by targeting an optimum absorption site. The needles are preferably arranged in the array with alternating lengths. Generally, the array includes microneedles having two different lengths. In other embodiments, the array can have needles of several lengths.

The device of the invention is generally designed to be a disposable device. The device can be used safely and effectively for intradermal delivery of a pharmaceutical agent or other substance. The device is particularly suitable for introducing a vaccine intradermally for efficiently delivering a small amount of the vaccine antigen for presentation to the Langerhans cells. The length, width and spacing of the needles can vary depending on the pharmaceutical agent being administered or required to pierce the stratum corneum to the optimum depth for the specific pharmaceutical agent being administered. When delivering a vaccine, the needles are dimensioned to target the optimum intradermal delivery site to promote the desired immune response.

The intradermal device of the present invention provides a reliable way to deliver individual and multiple pharmaceutical agents in small doses by an intradermal route. The microneedles of the delivery device limit the penetration of the needles to prevent inadvertent deep penetration into the tissue as in conventional needles. The microneedles are also less painful to the patient and exhibit a lower incidence of skin necrosis common with some DNA vaccines. The multiple chambers of the delivery device enable the administration of multiple vaccines and pharmaceutical agents simultaneously without reformulation or combination of the pharmaceutical agents. Administering the pharmaceutical agents through the skin provides efficient presentation of antigen or vaccine, thereby reducing the dose of the vaccine delivery. The delivery device is particularly suitable for DNA vaccines that may be a stable dry protein product.

Figure 8:
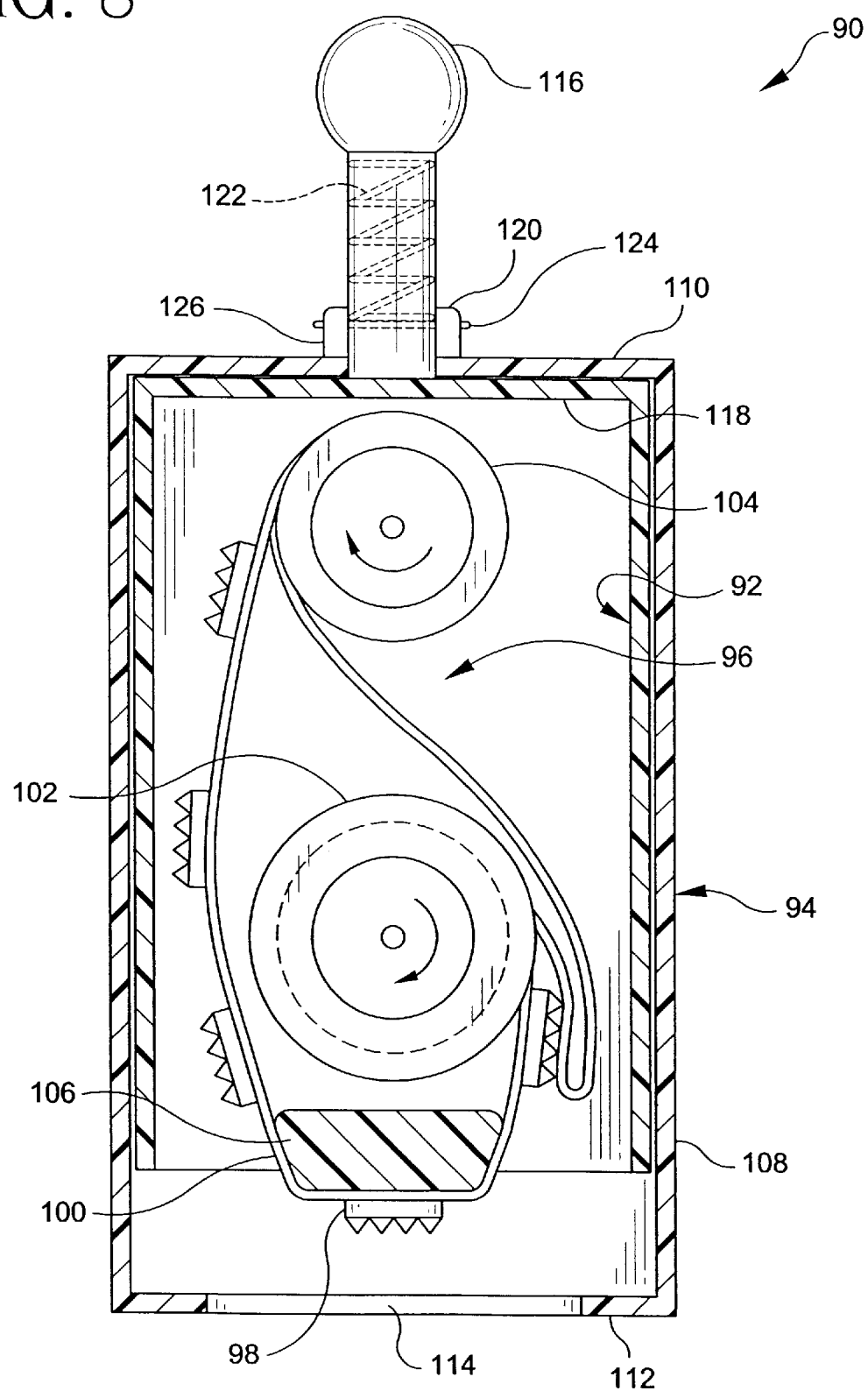
FIG. 8 is a cross-sectional side view of the device in a further embodiment of the skin penetrating members in a retracted position.
Figure 9:
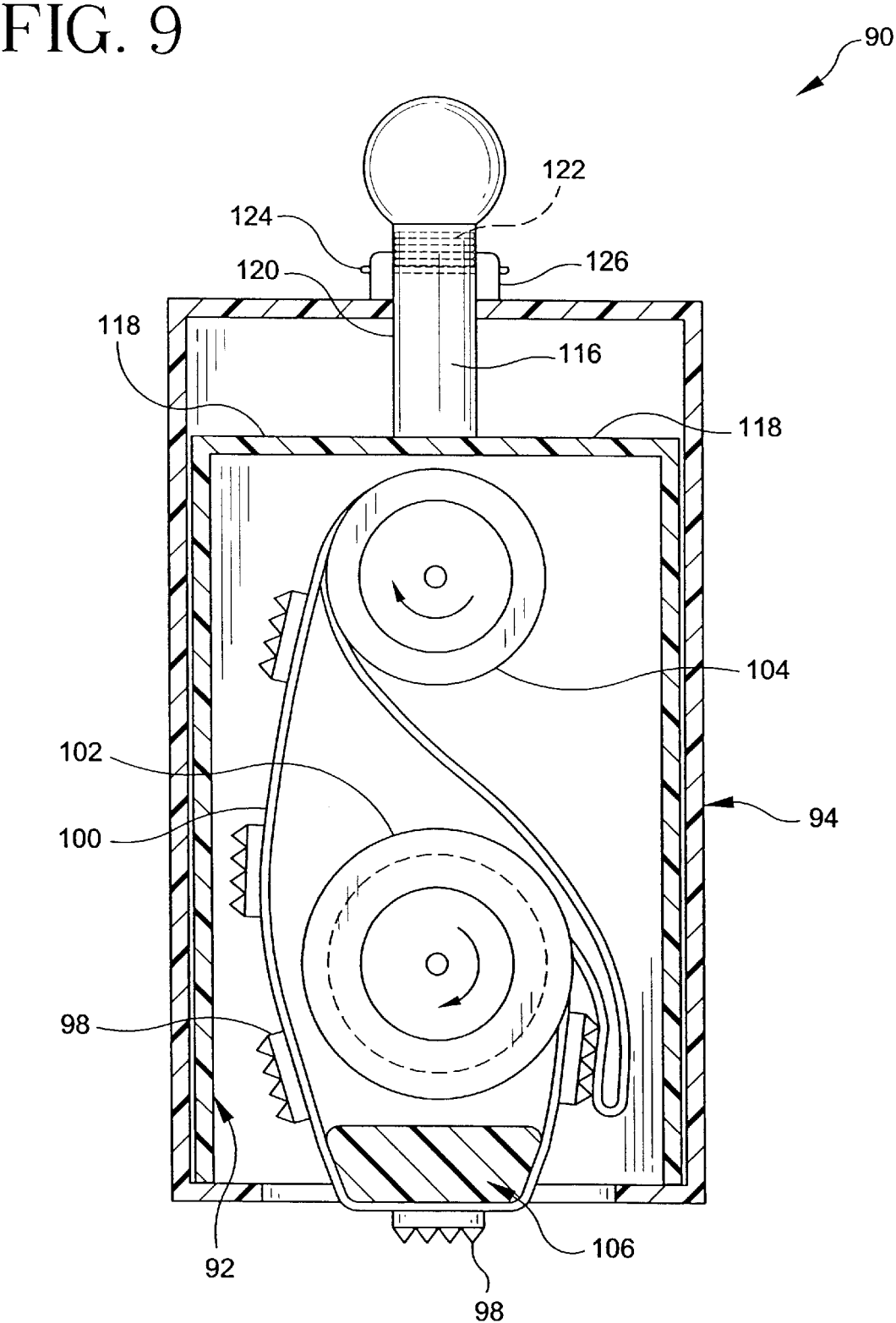
FIG. 9 is a cross-sectional view of the device of FIG. 8 shown the skin penetrating device projecting from the housing.

Embodiment of FIGS. 8 and 9

In a further embodiment shown in FIGS. 8 and 9, device 90 includes an inner support carriage 92 mounted within a housing 94. As shown in FIG. 8, carriage 92 supports a supply 96 of skin penetrating devices 98 attached to a web 100. As in the previous embodiment, web 100 can be advanced from a supply spool 102 to receiving spool 104 such that web 100 and skin penetrating devices are sequentially advanced to an operating position over a platen 106 attached to carriage 92.

Carriage 92 is enclosed within housing 94 for reciprocal movement. Housing 94 includes side walls 108, a top wall 110, and a bottom wall 112. Bottom wall 112 includes an opening 114 having dimensions to allow one skin penetrating device 98 to protrude through opening 114. Housing 94 can include slots on opposite walls for receiving guide pins (not shown) coupled to carriage 92 to provide limited sliding movement of carriage 92 within housing 94. Preferably, carriage 92 is spring biased away from opening 114 of housing 94 to the position shown in FIG. 8.

A handle 116 is coupled to a top end 118 of carriage 92 and extends through an opening 120 in top wall 110 of housing 94. In one embodiment, handle 116 is hollow and encloses a coil spring 122. Spring 122 has a top end that abuts the top end of handle 116 and a lower end that abuts a fixed pin 124 mounted in a collar 126 on top wall 110. Handle 116 includes an elongated slot (not shown) extending in a longitudinal direction for receiving pin 124 and enabling handle 116 to slide with respect to housing 94.

As shown in FIG. 8, spring 122 biases handle 116 in an upward direction with respect to housing 94 and biases carriage 92 away from bottom wall 112 and opening 114. In the position shown in FIG. 8, skin penetrating devices 98 are retracted within housing 94 to prevent inadvertent contact with skin penetrating devices 98. A downward pressure on handle 116 moves carriage 92 downward into an operating position as shown in FIG. 9 where skin penetrating device 98 is presented in opening 114 for contact with the skin of a patent. Releasing the pressure of handle 116 retracts carriage 92 and skin penetrating device 96 back into housing 94.

As in the previous embodiment, an advancing assembly is provided to advance web 100 to present a fresh skin penetrating device for each use. The advancing assembly can be a handle or crank extending through the side walls of carriage 92 and housing 94 and coupled to the receiving or supply spools. In further embodiments, carriage 92 can be provided with a suitable ratcheting mechanism as known in the art that is able to incrementally advance the web with each reciprocating cycle of carriage 92.

While several embodiments have been shown to illustrate the present invention, it will be understood by those skilled in the art that various changes and modifications can be made therein without departing from the scope of the invention as defined in the appended claims.

What is claimed is:

1. A device for intradermally withdrawing or delivering a substance to a patient, said device comprising:
   a support having a top end, and a bottom end;
   a plurality of spaced apart skin penetrating devices,
   an advancing assembly for incrementally advancing said skin penetrating devices to said bottom end of said support to a position where at least one of said skin penetrating devices faces outwardly from said bottom end of said support in an operating position for withdrawing a substance or delivering a substance to a patient.

2. The device of claim 1, said support comprising a bottom wall having at least one opening, and wherein said advancing assembly directs said skin penetrating devices through said at least one opening to said operating position.

3. The device of claim 2, further comprising a flexible web having an outer face, a first end and a second end, wherein said skin penetrating devices are attached to said outer face of said web.

4. The device of claim 3, wherein said bottom wall of said support includes a first and second opening, wherein said web extends outwardly through said first opening from an interior of said support and through said second opening into said support.

5. The device of claim 4, wherein said bottom wall includes a platen, said first opening being situated on a first side of said platen and said second opening being situated on a second side of said platen, wherein said advancing assembly advances said web over said platen whereby each of said skin penetrating devices is successively oriented over said platen in said operating position.

6. The device of claim 3, further comprising a supply member in said support for supplying said web.

7. The device of claim 6, wherein said supply member is a supply spool rotatably mounted in said support and said first end of said web is coupled to said supply spool.

8. The device of claim 4, further comprising a receiving member for receiving said web after passing through said second opening in said support.

9. The device of claim 8, wherein said receiving member is a take-up spool rotatably mounted in said support and said second end of said web being coupled to said take up spool.

10. The device of claim 1, wherein each of said skin penetrating devices includes a base and a plurality of skin penetrating members extending from said base.

11. The device of claim 1, wherein each of said skin penetrating devices is a microneedle array.

12. The device of claim 9, wherein said advancing assembly further comprises a handle coupled to said take-up spool for rotating said take-up spool and advancing said skin penetrating members to said operating position.

13. The device of claim 3, wherein said web includes a protective cover overlying said skin penetrating members, and wherein said device includes a device for removing said protective cover from said skin penetrating members before advancing said web and skin penetrating member to said operating position.

14. The device of claim 1, further comprising a housing, wherein said housing has an open end and said support is reciprocally mounted within said housing from a first position where said support and skin penetrating device are retracted from said open end to a second position where at least one of said skin penetrating devices extends from said open end a distance sufficient for contacting the skin of a patient.

15. The device of claim 14, wherein said support is spring biased away from said open end of said housing.

16. An intraepidermal device for withdrawing or delivering a substance though the skin of a patient, said device comprising:

a support having a top end, and a bottom end and a bottom wall at said bottom end;

a supply member for supporting a web having a plurality of spaced apart skin penetrating devices;

a receiving member for receiving said web; and an advancing assembly for incrementally advancing said web from said supply member across said bottom wall of said support to said receiving member, wherein each of said skin penetrating devices are available for penetrating the skin of a patient when positioned on said bottom wall.

17. The device of claim 16, wherein said supply member is a supply spool and said web is wound on said supply spool.

18. The device of claim 16, wherein said receiving member is a take-up spool.

19. The device of claim 18, wherein said advancing assembly rotates said take-up spool to wind said web onto said spool and to pull said web across said bottom wall.

20. The device of claim 19, wherein said web comprises a cover sheet overlying said skin penetrating devices, wherein said sheet has a longitudinal end coupled to said take-up spool whereby rotation of said take-up spool separates said cover sheet from said web and skin penetrating devices while advancing said skin penetrating devices to said bottom wall.

21. The device of claim 16, wherein said bottom wall includes a platen.

22. The device of claim 16, wherein said substance is a coating on said skin penetrating devices.

23. The device of claim 16, wherein said skin penetrating device includes a base and a plurality of skin penetrating members on said base.

24. The device of claim 16, wherein each of said skin penetrating devices is a microneedle array.

25. The device of claim 24, wherein said microneedle array has a plurality of microneedles of about 50 microns to about 2,000 microns in length.

26. The device of claim 16, further comprising a housing, wherein said housing has an open end and said support is reciprocally mounted within said housing from a first position where said support and skin penetrating device is retracted from said open end to a second position where at least one of said skin penetrating devices extends from said open end a distance sufficient for contacting the skin of a patient.

27. The device of claim 26, wherein said support is spring biased away from said open end of said housing.

28. The device of claim 16, wherein each of said skin penetrating devices is a microneedle array machined from a silicon substrate.

29. The device of claim 28, wherein said microneedles have a substantially square cross-section and a beveled tip.

30. The device of claim 28, wherein a hollow passage extends axially through said microneedles.

31. The device of claim 30, wherein said array of microneedles is mounted on said web such that said hollow passages forms a reservoir.

32. A method of withdrawing or delivering a substance to a patient comprising the steps of providing a device including a support having a top end, bottom end and a bottom wall, a plurality of spaced apart skin penetrating devices, and an advancing assembly for incrementally advancing said skin penetrating devices to said bottom end of said support to a position where at least one of said skin penetrating devices faces outwardly from said bottom end of said support in an operating position for withdrawing a substance or delivering a substance to a patient, advancing said skin penetrating devices to present a clean skin penetrating device on said bottom wall to an operating position in a generally downwardly facing direction, and pressing said device and skin penetrating device against the skin of a patient with sufficient force to penetrate said skin and withdraw or deliver a substance through said skin.

33. The method of claim 32, further comprising advancing a spent skin penetrating device to a receiving member, and advancing a clean skin penetrating member to said operating position.

34. The method of claim 32, wherein said support includes a bottom wall with a first opening and a second opening, and a flexible web having said skin penetrating device attached to an outer face of said web, said web having a first end coupled to said advancing assembly, wherein said method comprises advancing said web through said first opening to said operating position and retracting said web having a spent skin penetrating member through said second opening.

35. The method of claim 34, wherein said advancing assembly further comprises a supply spool having a first end of said web attached thereto and a take-up spool having a second end of said web attached thereto, said method comprising rotating said take-up spool to advance said web and skin penetrating device to said operating position.

36. The method of claim 32, wherein said skin penetrating devices comprise an array of skin penetrating members.

37. The method of claim 36, wherein said array of skin penetrating members include a substance to be delivered to a patient, said method comprising pressing said skin penetrating members against the skin of a patient to penetrate said skin and deliver said substance.

38. The method of claim 36, wherein said skin penetrating members are hollow needles, and said method comprises pressing said needles against the skin of a patient to penetrate said skin and withdraw a substance from said skin.

* * * * *